United States Patent
Rabal

(12) 
(10) Patent No.: US 6,394,805 B1
(45) Date of Patent: May 28, 2002

(54) DENTAL CROWN REMOVER WITH BASKET

(76) Inventor: Jennifer L. Rabal, 1016 Meridith Dr., Terrell, TX (US) 75160-5023

( * ) Notice: Subject to any disclaimer, the term of this patent is extended or adjusted under 35 U.S.C. 154(b) by 0 days.

(21) Appl. No.: 09/704,065

(22) Filed: Nov. 1, 2000

Related U.S. Application Data

(60) Provisional application No. 60/164,425, filed on Nov. 9, 1999.

(51) Int. Cl.$^7$ .................................................. A61C 3/14
(52) U.S. Cl. .......................... 433/159; 606/205; 81/418
(58) Field of Search ................................. 433/159, 160, 433/4; 606/205; 81/418

(56) References Cited

U.S. PATENT DOCUMENTS

| | | | | |
|---|---|---|---|---|
| 1,487,776 A | * | 3/1924 | Goldberg | |
| 1,626,226 A | * | 4/1927 | Cantor | |
| 2,504,227 A | * | 4/1950 | Rubba | |
| 2,592,641 A | * | 4/1952 | Balderstone | |
| 2,725,632 A | * | 12/1955 | Rabben | |
| 3,834,026 A | | 9/1974 | Klein | |
| 4,040,186 A | * | 8/1977 | Kalveliage | |
| 4,697,483 A | * | 10/1987 | Rogers | 81/418 |
| 5,182,841 A | * | 2/1993 | Park et al. | 29/229 |
| 5,538,421 A | * | 7/1996 | Aspel | 433/159 |
| 5,833,460 A | * | 11/1998 | Maeda | 433/159 |
| 5,893,876 A | * | 4/1999 | Turkel et al. | 606/205 |

OTHER PUBLICATIONS

Sullivan–Schein Dental Catalogue; pp. 284–285; (undated).

* cited by examiner

Primary Examiner—Ralph A. Lewis
(74) Attorney, Agent, or Firm—Chauza & Handley, L.L.P.

(57) ABSTRACT

A dental device for removing a temporary or non-cemented crown. The device includes pliers-type handles for operating a corresponding pair of tips. The tips are equipped with grips for holding therebetween a temporary or non-cemented permanent crown. Fastened to at least one of the tips, and moveable therewith, is a basket for catching the crown should it become dislodged from the grips.

23 Claims, 7 Drawing Sheets

DENTAL CROWN REMOVER WITH BASKET

CROSS-REFERENCE TO RELATED APPLICATION

This application claims the benefit of U.S. Provisional Application entitled "Dental Crown Remover," filed Nov. 9, 1999 and accorded Ser. No. 60/164,425, the entire disclosure of which is incorporated herein by reference.

TECHNICAL FIELD OF THE INVENTION

This invention relates in general to dental devices, and more particularly to the type of devices for removing temporary crowns.

BACKGROUND OF THE INVENTION

Significant advances have been made in the last few decades in the care and treatment of people's teeth. Not only are there a host of personal teeth care appliances and teeth cleaning agents, but significant advances have also been made in the general practice and general dentistry field. It has become a common practice to repair teeth by placing a crown or artificial tooth structure over the existing (remaining) nondecayed structure. The original tooth is generally prepared by grinding a major portion of the tooth away, leaving only the remaining structure. A mold is made of the prepared tooth structure, so that a crown can be fabricated. In the meantime, the patient is fitted with a temporary crown so that normal chewing functions can be carried out during the time in which the permanent crown is made. A crown remover of this type is described in detail in U.S. Pat. No. 3,834,026.

During the procedure in fitting the temporary crown and grinding the original tooth structure, numerous attempts are generally made to fit the temporary crown on the remaining tooth structure, as far as height and concavity are concerned. In doing so, various types of pliers and other appliances have been constructed so as to firmly grip the temporary crown for placement on the remaining tooth structure. The pliers generally include a rounded set of jaws to firmly grip the crown so as to fit it on the remaining tooth structure, as well as remove it for grinding adjustments to either the remaining tooth structure or the temporary crown.

Frequently, in the placement or removal of the temporary crown from the remaining tooth structure, the crown inadvertently loses its grip from the pliers, and falls or otherwise becomes dislodged in the patient's mouth. In other more serious occurrences, the patient can inadvertently swallow or aspirate the crown. This is especially troublesome when the crown fitting operation is carried out on the upper teeth of a patient. The occurrences with which the temporary crowns are inadvertently dropped in the patient's mouth are frequent during the training of dental students.

Pliers-type appliances that are forged to be short are not often used for the reason that they cannot easily access a patient's teeth with an unobstructed view, especially the posterior teeth.

It can be seen from the foregoing, that a need exists for a technique for easily recovering a dropped crown so that it does not fall in the patient's mouth. Another need exists for a dental appliance that is long and forged for easier access and that is equipped with a basket for catching a dislodged crown to prevent it from falling into the patient's mouth. Another need exists for a dental appliance that can deflect or catch a crown, onlay or other similar device dislodged from the dental appliance. Another need exists for a crown remover that allows easier access in a patient's mouth to posterior teeth for installing and removing a crown thereon. Yet another need exists for various crown grips shaped to facilitate the removal of crowns. An additional need exists for a crown remover adapted for removably attaching various tips thereto, where the tips have different shaped crown grips.

SUMMARY OF THE INVENTION

In accordance with the principles and concepts of the invention, there is disclosed a dental appliance for reducing those occurrences in which a dislodged or dropped crown falls within the patient's mouth. According to a preferred embodiment of the invention, a pliers appliance includes a pair of handles that can be gripped by the dentist, with jaws at the opposing ends shaped to conform to the crown curvature to firmly grip it. In accordance with an important feature of the invention, at least one of the jaws of the pliers appliances includes a basket structure for catching or deflecting the crown, should it fall or become dislodged from the jaws of the appliance.

In accordance with another feature of the invention, the basket structure is constructed of a flexible wire mesh so as to flex during opening and closing of the jaws of the pliers appliance.

In yet another embodiment of the invention, a tip of the appliance is constructed to include a grip that is shaped to grasp an onlay for applying the same to a tooth. The onlay tip of the invention is planar so that the shape thereof can grip the onlay structure without the tooth itself interfering with installing the onlay on the tooth.

The many embodiments may include various tips removably attached thereto, where each tip can have a different shaped crown grip. The various crown grips are shaped to facilitate different shaped crowns, onlays, etc.

BRIEF DESCRIPTION OF THE DRAWINGS

Further features and advantages will become apparent from the following and more particular description of the preferred and other embodiments of the invention, as illustrated in the accompanying drawings in which like reference characters generally refer to the same parts, components, elements or functions throughout the views, and in which.

DETAILED DESCRIPTION OF THE INVENTION

Figure 1:
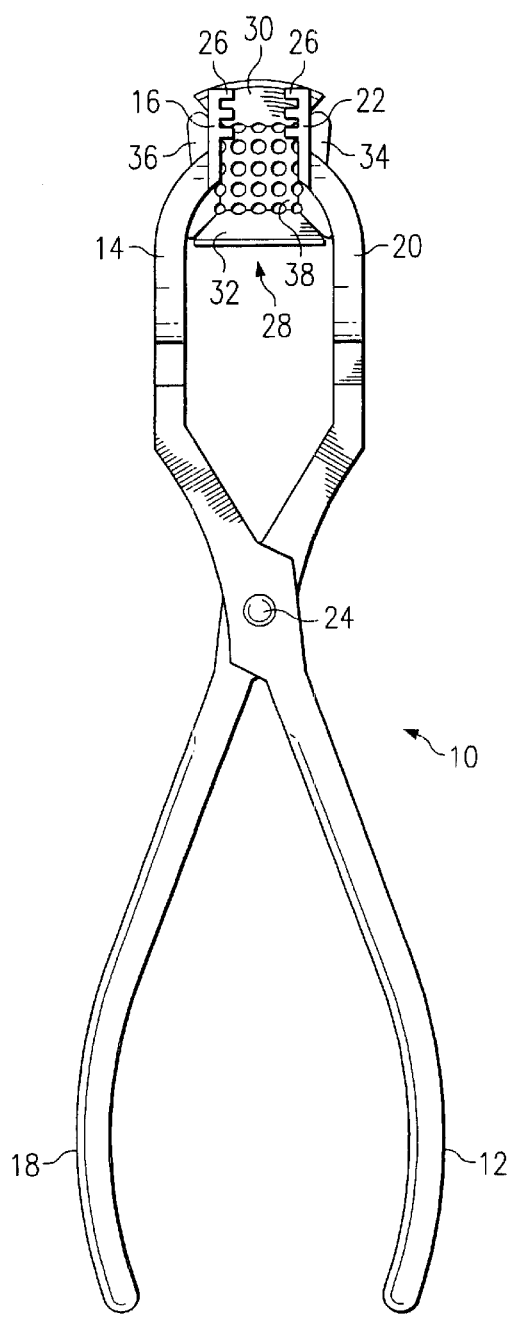
FIG. 1 illustrates a top view of the crown remover constructed according to one embodiment of the invention.

FIGS. 1–4 illustrate various views of the crown remover constructed according to one embodiment of the invention. As used herein, the term "crown" also encompasses the term only, bridge and other fixtures that are applied to a patient's teeth or other tissue. The crown remover 10 includes a pliers-type appliance, having a first member defined by a handle 12 at one end and a tip 14 at the other end. The end of the tip 14 is equipped with a crown grip 16. The other member similarly includes a handle 18, a tip 20 and a crown grip 22. The first member and second member are pivotally joined at respective midsections thereof, by a screw 24, rivet, pin or other pivotal or hinging mechanism. As is conventional with pliers-type tools, the handles 12 and 18 can be manipulated by the user to open and close the tips 14 and 20. The crown grips 16 and 22 are adapted for firmly gripping the crown to both install it on the margin structure, and remove it therefrom. As noted above, this is especially important for use in fitting temporary crowns until the permanent crown can be applied next to the tooth margin structure. The crown grips 16 and 22 each include plural fingers 26 at the ends thereof to provide a certain degree of flexibility in gripping the crown. The fingers 26 of each of the crown grips 16 and 22 are angled inwardly toward each other. This facilitates the removal of a temporary crown by allowing the inwardly bent fingers 16 to grasp the marginal edge of the crown. When pulled, the crown is more firmly grasped for removal.

Figure 4:
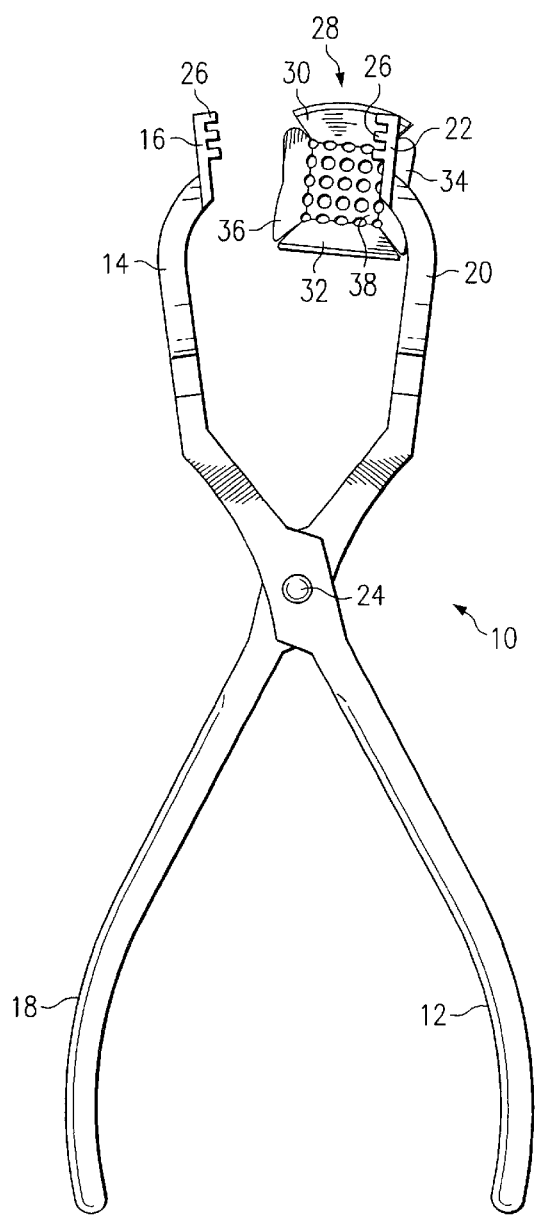
FIG. 4 illustrates a top view of the crown remover shown in FIG. 1, but with the gripping tips shown separated.

In accordance with an important feature of the invention, one of the tips 14 or 20 is equipped with a container or basket 28 that moves with the tip as the crown remover 10 is manually manipulated. In the preferred form, the basket 28 is fastened to the tip 20. The basket 28 is constructed with four sidewalls that slant or taper outwardly as shown in FIG. 2. The front and back sidewalls 30 and 32 are somewhat taller or higher than the other sidewalls 34 and 36, as shown in FIGS. 2 and 4. Each of the four sidewalls 30–36 of the basket 28 is joined at the bottom edges thereof to a basket bottom 38 which is perforated so as not to be water tight. While the basket 28 constructed according to the illustrated embodiment of FIGS. 1–4 is generally rectangular shaped, other shapes can be utilized with equal effectiveness. For example, square, round, oval and other shapes of baskets can be utilized.

Figure 2:
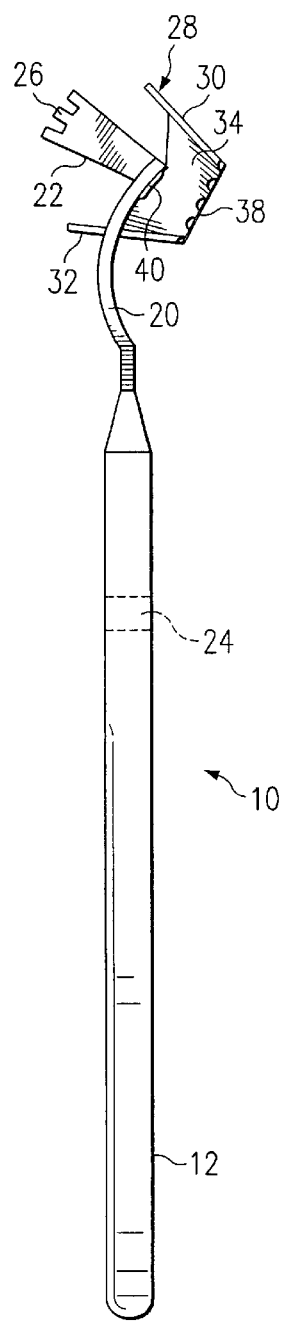
FIG. 2 illustrates a side view of the crown remover shown in FIG. 1.
Figure 3:
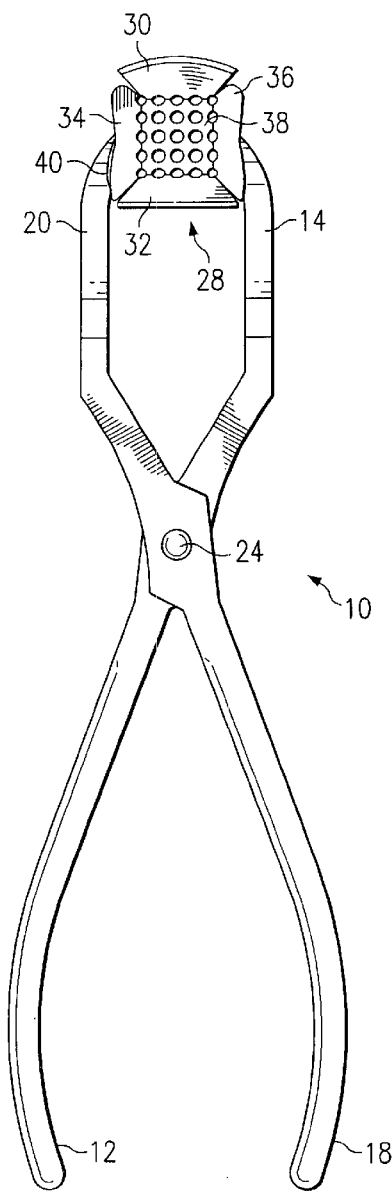
FIG. 3 illustrates a bottom view of the crown remover shown in FIG. 1.

When viewing the crown remover 10 from the top, as shown in FIG. 1, the tip 20 is welded or otherwise bonded to the right-hand sidewall 34 of the basket 28. The weld is placed in the area shown in FIG. 2 by reference numeral 40. With this construction, the basket 28 is fixed to one tip 20 and moves therewith, as shown in FIG. 4. The basket 28 can be attached to the tips 20 by other means, such as by the use of screws inserted in holes in the basket, and tightened in threaded holes in the tip 20. In other arrangements, the basket can be fixed to the crown grip 22, or to the other tip 14 or grip 16.

With reference again to FIGS. 1 and 2, the basket 28 is generally larger than the crown grips 16 and 22. Hence, should the crown fall, it has a better chance of dropping into the basket 28. The pliers appliance 10 is not limited to use in installing crowns or onlays on a patient's upper teeth, but also the lower teeth. In this latter instance, the basket 28 can function to deflect a crown that is propelled upwardly when installing or removing the same. While the basket 28 cannot catch and hold a crown when inverted, such as when used on a patient's bottom teeth, the basket 28 can deflect a propelled crown so that it does not enter the patient's air passageways.

The crown remover 10 is preferably constructed by forging techniques with a stainless steel or other suitable material. The crown remover 10 can thus be sterilized by conventional sterilization equipment.

In operation, a dentist can open the tips 14 and 20 of the pliers appliance 10 and insert a permanent or temporary crown, or onlay, between the crown grips 16 and 22. Holding the crown firmly between the grips 16 and 22 by applying pressure to the handles 12 and 18, the dentist can engage the crown with the margin structure previously prepared. The crown remover 10 is particularly advantageous when installing permanent or temporary crowns in the top teeth of a patient. In this. instance, should the crown fall, become dislodged or otherwise disengaged from the tooth structure, and falls, the basket 28 will catch the crown and prevent its falling into the patient's mouth. In the event a temporary crown has been applied to the tooth structure, and needs removal thereof, the dentist can grasp the temporary crown with the crown grips 16 and 22 and wiggle the temporary crown until it becomes loosened from the tooth structure. Again, should the temporary crown either become dislodged from the grips 16 and 22, or should it break into pieces, the crown, tooth or parts thereof will fall into the basket 28. This is highly important in preventing parts of the crown or tooth from falling into the patient's mouth, or down the patient's throat with the possible risk of being aspirated into the lungs. The appliance 10 is utilized in the same manner with permanent crown or onlays.

Figure 5A:
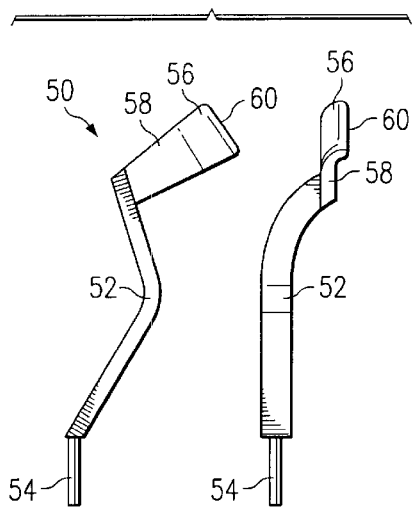
FIGS. 5a–5d illustrate various embodiments of crown grips, each adapted for gripping different types of crowns.

FIGS. 5a–5d illustrate different tips adapted for use with the invention. The various tips are adapted for being removably attached to the dental appliance described below. FIG. 5a illustrates one embodiment of a crown remover tip 50 in a side view shown at the left of the drawing, and taken orthogonal thereto in the right of the drawing. The tip 50 includes the dog-leg tip 52 having an end 54 removably attached to the pliers. The dog-leg tip 52 provides better access to the posterior teeth of a patient. In addition, a better unobstructed view of the teeth is provided, even with the appliance positioned in the patient's mouth. At the other end of the tip 52 is a crown grip 56. The grip 56 includes a generally planar blade 58 with an end 60 that is bent or otherwise curved inwardly to capture the crown. With this arrangement, the grip 56 can engage the crown and partially envelope the same.

Figure 5B:
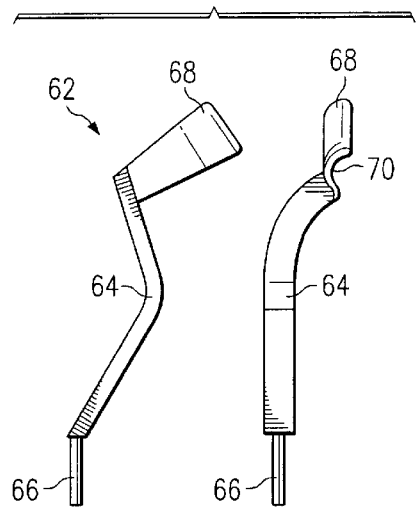

FIG. 5b illustrates another embodiment 62 having a dog-leg tip 64 with an end 66 that is removably attached to the dental device. The crown grip 68 is generally shaped with a concave inside surface 70 to again envelope and grip the crown.

Figure 5C:
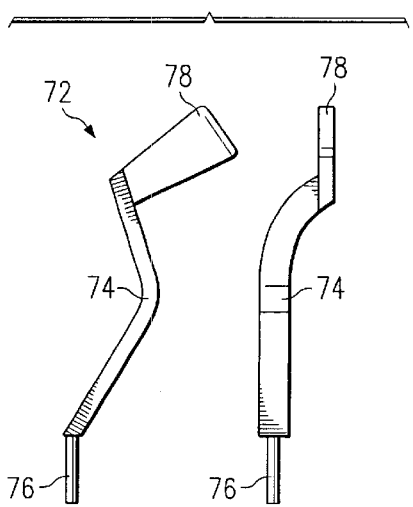

FIG. 5c illustrates yet another embodiment of a tip 72. The tip 72 includes a dog-leg mid-section 74 and an end 76 that is constructed to be removably attached to the dental device. A crown grip 78 is constructed so as to be generally planar. This embodiment is well adapted for use with onlays to firmly grip the same.

Figure 5D:
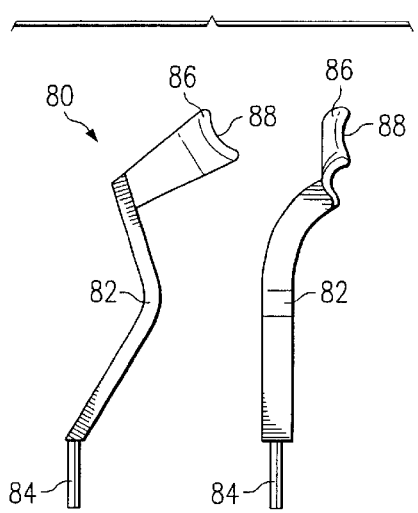

FIG. 5d illustrates yet another embodiment of a tip 80. The tip 80 includes a dog-leg shaped mid-section 82 with an end 84 that is removably attachable to the dental device. The crown grip 86 is much like that shown in FIG. 5b, but includes an end 88 that is curved inwardly. This curved end 88 facilitates the manipulation of a crown with respect to other teeth in the patient's mouth.

In all of the embodiment of the various tips shown in 5a–5d, such tips can be utilized in combination with a basket structure described below, both of which are removably attached to the dental device.

Figure 6:
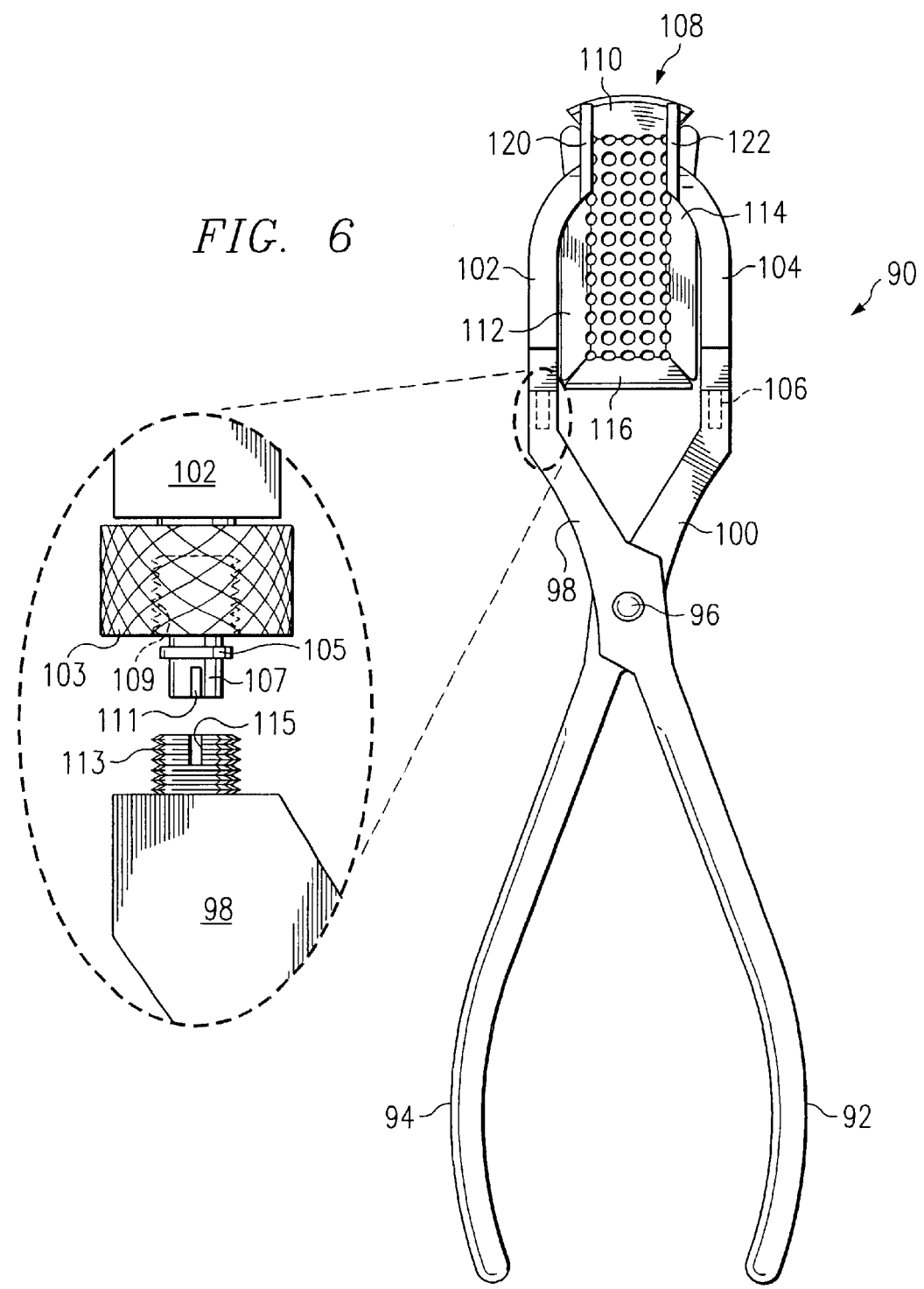
FIG. 6 illustrates a top view of a crown remover constructed according to another embodiment of the invention, in which the gripping tips are removably attached to the pliers, and showing in the enlargement the mechanism allowing the parts to be removably attached together.
Figure 7:
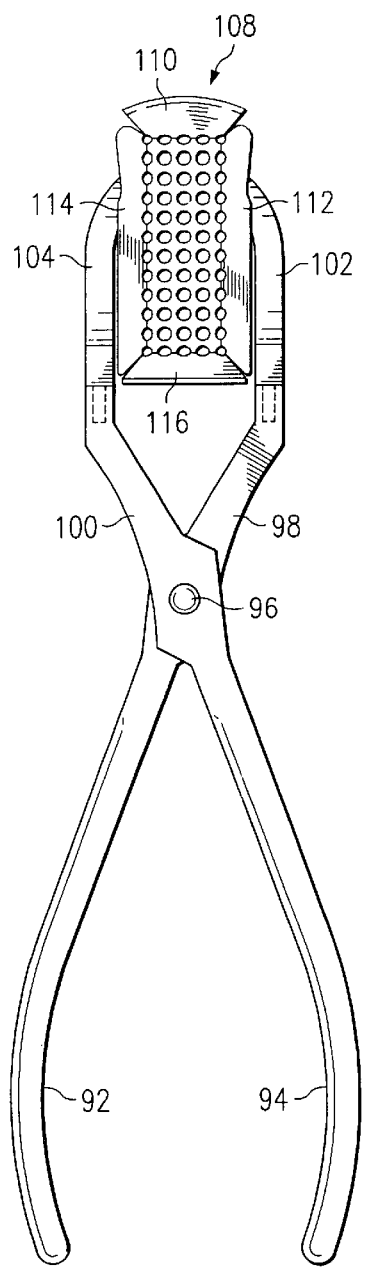
FIG. 7 illustrates a bottom view of the embodiment shown in FIG. 6.
Figure 8:
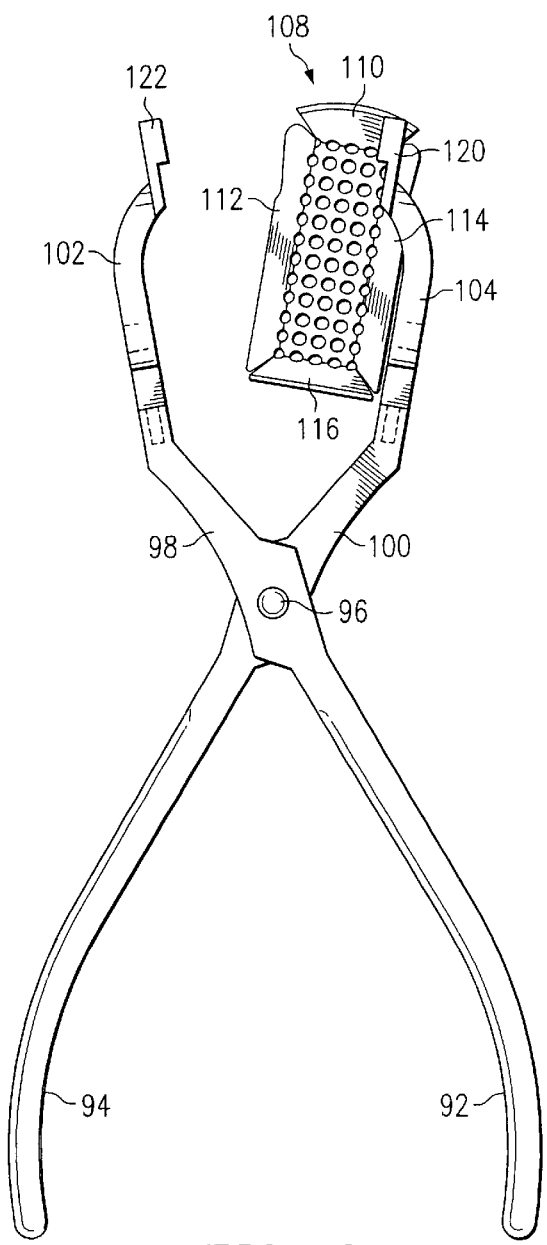
FIG. 8 illustrates a top view of the embodiment shown in FIG. 6, with the gripping tips shown separated, and removable from the pliers.

With reference now to FIGS. 6–8, there is illustrated another embodiment of the dental device constructed according to the principles and concepts of the invention. The dental device 90 is constructed as a pliers-like appliance having handles 92 and 94 pivotally connected together by a screw 96, or the like. Connected at a working end of the handle 92 is a shortened tip 98. In like manner, connected to the working end of the other handle 94 is a shortened tip 100. Corresponding tip extensions 102 and 104 are connected respectively to the shortened tips 98 and 100. The mechanism for removably attaching the tip extensions to the respective shortened tips is diagrammatically shown as reference numeral 106. Both tip extensions 102 and 104 are removably attached to the pliers appliance 90 in the same manner. Fastened to one tip extension is an elongate basket 108, shown in FIG. 8 connected to tip extension 104. The basket 108 is constructed substantially identical to that shown in FIGS. 1–4, except the basket 108 is rectangular-shaped. The end sidewall 110 is longer than the other sidewalls 112–116. This facilitates capturing of a dropped or dislodged crown so that it is not directed toward the patient's throat. The dental device 90 otherwise functions in a manner much like that described above in connection with FIGS. 1–4. The crown grips 120 and 122 can be any of the types shown in FIGS. 5a–5d or yet other configurations for gripping the particular type of fixture to be fastened or otherwise attached to a patient's tooth.

The principles and concepts of the invention can also be utilized for capturing or deflecting body tissue parts while carrying out operations thereon.

The enlargement shown in FIG. 6 illustrates the mechanism which allows the tips 102 and 104 to be removably attached to the corresponding shortened tips 98 and 100. In the preferred form, the mechanism includes a conventional threaded coupling screw arrangement and registration means to maintain alignment between the shortened tip 98 and the appliance tip 102. The removable attachment mechanism includes an internally threaded sleeve 103 on the tip 102. The sleeve 103 is captured on the tip 102 by an annular collar 105 formed integral with the tip 102. The tip 102 has a rib 111 or raised area to provide registration and alignment between the tip 102 and the shortened tip 98. The rib 111 is formed on a stub end 107 of the tip 102. The stub 107 fits within a receptacle 113 formed within the shortened tip 98. The receptacle 113 has formed therein a registration slot 115 for receiving therein the rib 111 of the tip 102. The outer surface of the receptacle 113 is threaded for engagement with the internal threads 109 of the sleeve 103.

The removable attachment mechanism is fastened together by aligning the rib 111 with the slot 115, and then sliding the stub 107 into the bore of the receptacle 113 until the collar 115 engages with the frontal edge of the receptacle 113. Then, the sleeve 103 is threadably engaged with the outer threads of the receptacle 113 until tight. This secures the tip 102 to the shortened tip 98 and prevents rotation therebetween.

Many other releaseable attachment mechanisms can be utilized with equal effectiveness. For example, the stub 107 can be square for fitting within a square bore of the receptacle 113.

Figure 9:
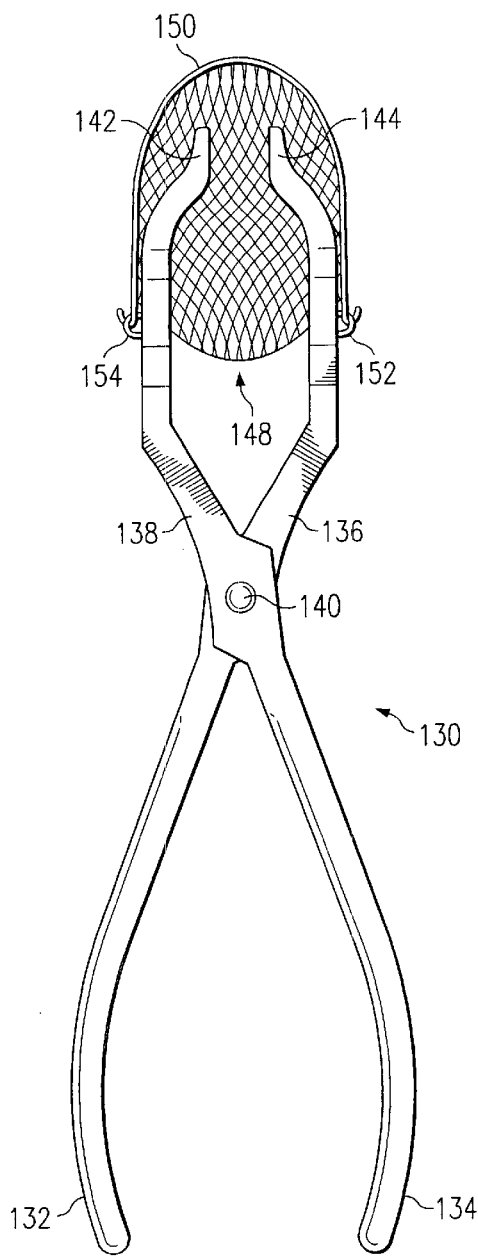
FIG. 9 is a top view of yet another embodiment of the dental device, equipped with a wire mesh basket.

FIG. 9 illustrates yet another embodiment of the invention. Here, a pliers-type appliance 130 includes a pair of handles 132 and 134 connected to respective tips 136 and 138 via a pivot pin 140. Formed at the end of the tips 136 and 138 are respective crown grips 144 and 142. In this embodiment, a flexible mesh basket 148 is fastened to the tips 136 and 138. The wire mesh is preferably constructed of a metallic link-type of flexible mesh. The support wire loop 150 and the mesh basket can both be formed with stainless steel material. The peripheral edge, or opening, of the wire mesh basket 148 is supported by a flexible support wire loop 150. The support wire loop 150 has ends that are hooked for engagement within corresponding loops 152 and 154 welded to the outer sides of the tips 136 and 138. With this arrangement, when the crown grips 142 and 144 are opened or closed, the mesh basket 148 flexes accordingly. In addition, the ends of the wire support 150 engaged within the loops 152 and 154 are not completely closed, thereby allowing the wire mesh basket 148 to be removed. If the removability of wire mesh basket 148 is of secondary importance, then the ends of the wire support 150 can be welded or otherwise bonded to the sides of the tips 136 and 138.

Figure 10:
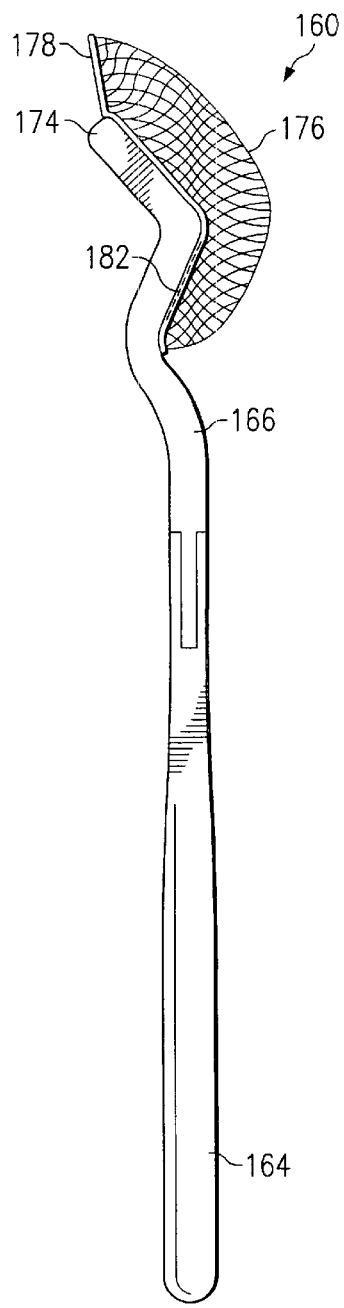
FIGS. 10 and 11 are respective side and bottom view of yet another embodiment of the dental device constructed according to the invention.
Figure 11:
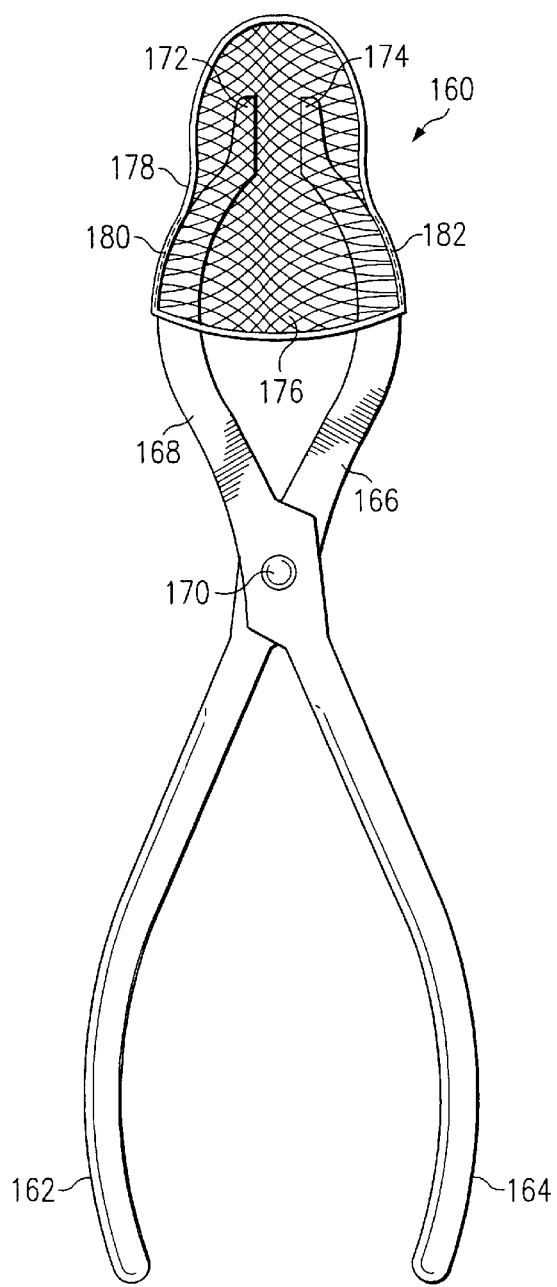

FIGS. 10 and 11 illustrate yet another embodiment of a crown remover 160. The crown remover 160 of this embodiment includes a pair of pliers-type handles 162 and 164 coupled to respective tips 166 and 168, via a pivot pin 170. Formed integral with the tips 166 and 168 are corresponding crown grips 172 and 174. A flexible mesh basket 176 has an opening supported by a wire loop 178 formed in the shape shown in FIGS. 10 and 11. The opening of the wire mesh basket 176 is welded or otherwise fixed to the wire loop 178. In addition, the wire loop 178 is welded to the tips 166 and 168 at locations 180 and 182. With this construction, the wire mesh basket 176 is fixed to the tips 166 and 168 of the device 160 and thus, moveable therewith when the device 160 is manipulated to open and close the grips 172 and 174. Other shapes of the basket 176 and wire loop 178 can be constructed for adapting it to various shapes of tips 166 and 168.

Figure 12:
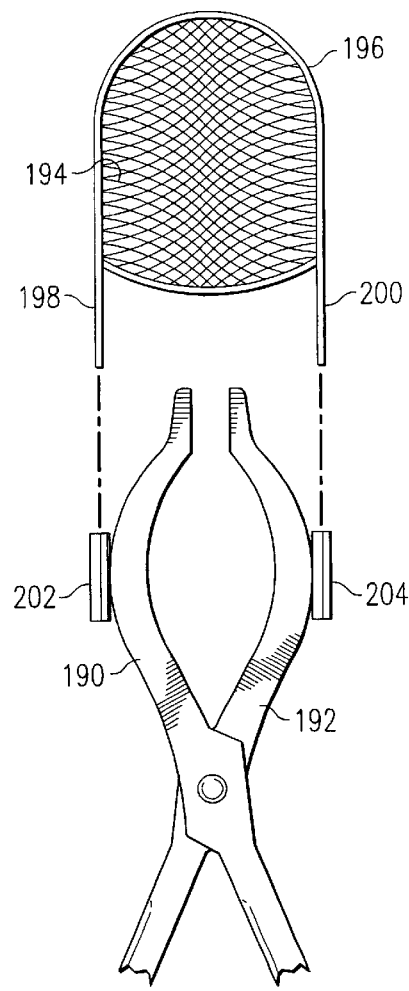
FIG. 12 is a top view of a portion of the dental device, constructed with a wire mesh basket removably attached thereto.

FIG. 12 illustrates another embodiment of the dental device according to the invention, in which there is provided a pair of tips 190 and 192, coupled to a plier-type device (not shown). A flexible wire mesh basket 194 has an opening or peripheral edge supported by a wire loop 196. The wire loop includes a pair of extensions 198 and 200 that are insertible into corresponding tubular receptacles 202 and 204. The tubular receptacles 202 and 204 are welded or otherwise bonded to the sides of the tips 190 and 192. This construction allows the device to be utilized without the basket 194 or, when the same is required, allows the basket wire ends 198 and 200 to be inserted into the tubular receptacles 202 and 204. Preferably, there is a friction fit between the wire ends 198 and 200 and the corresponding tubular receptacles 202 and 204.

Although the preferred and other embodiments have been described in detail, it should be understood that various changes, substitutions and alterations can be made therein without departing from the spirit and scope of the invention as defined by the appended claims.

What is claimed is:

1. A dental device for holding a crown, comprising:
 a pliers having a pair of handles for operating a corresponding pair of tips;
 a grip attached to each said tip such that when the handles of said pliers are manipulated, said grips move in a horizontal plane, said grips adapted for grasping a crown; and a basket attached to said pliers for engaging a crown that has been dislodged from said grips, said basket suspended under both said grips when a crown is grasped by said grip; and when said grips are moved in said horizontal plane.

2. The dental device of claim 1, wherein said basket is attached to one said tip.

3. The dental device of claim 2, wherein said basket is removably attached to said one tip.

4. The dental device of claim 1, wherein said basket is constructed of a wire mesh.

5. The dental device of claim 1, wherein at least a portion of said basket is constructed with at least a portion thereof which is perforated.

6. The dental device of claim 1, wherein at least one said tip is removably attached to said pliers.

7. The dental device of claim 6, wherein said tip is threadably engaged with said pliers.

8. The dental device of claim 6, wherein said tip is removably attached to said pliers.

9. The dental device of claim 1, wherein both said tips are removably attached to said pliers.

10. The dental device of claim 1, wherein said basket is attached to said pliers to underlie said grips when said grips hold a crown therebetween.

11. The dental device of claim 1, wherein said tips each have a dog-leg shape.

12. The dental device of claim 1, wherein said basket includes a circumferential sidewall and a bottom.

13. The dental device of claim 12, wherein at least one sidewall is longer than the remaining sidewalls, as measured upwardly from the bottom of the basket.

14. The dental device of claim 13, wherein said longer sidewall is a sidewall facing a patient's throat when the device is inserted in the patient's mouth.

15. A dental device for holding a crown, comprising:

a pair of handles coupled via a vertical pivotal axis to a corresponding pair of tips, whereby said tips are moved in a horizontal plane;

a grip attached to each said tip, said grips adapted for gripping a crown therebetween; and a container fastened to said device for holding a crown, said container having an opening positioned so as to underlie both said grips when said grips are moved together in a horizontal plane and have a crown gripped therebetween.

16. The dental device of claim 15, wherein said container is removably attached to said dental device.

17. The dental device of claim 15, wherein said container is constructed so as to be attached to one said tip.

18. The dental device of claim 15, wherein said container comprises a wire mesh basket.

19. The dental device of claim 15, wherein said container includes a basket defined by a flat perforated bottom, and four sidewalls extending upwardly therefrom, and angled outwardly.

20. A dental device for holding a crown, comprising:

a pliers having a pair of handles pivotal with respect to each other, and a tip attached to an opposite end of each said handle;

each said tip having attached thereto a grip adapted for gripping a crown for removing the crown from an upper tooth of a patient;

each said grip being attached to a respective said tip so that when said handles are manipulated in a horizontal plane, the grips project upwardly from the respective tips, a crown-gripping end of each said grip being curved inwardly toward each other; and a basket attached to said dental device and underlying said grips so as to catch a crown dislodged for said grips.

21. The dental device of claim 20, wherein said grips each include a plurality of fingers, the fingers associated with one grip being curved inwardly toward the fingers of the other grip, said fingers being adapted for gripping a crown.

22. The dental device of claim 20, wherein said basket is attached to one said tip and moves with the tip attached thereto when a respective said handle is pivotally moved.

23. A method of handling a crown using a dental device formed as a pair of pliers having a pair of crown grips and a basket attached to said pliers, comprising the steps of:

manipulating handles of the pliers in a horizontal plane to grasp a dental crown in the grips, and at the same time suspending the basket from said dental device under the gripped crown;

moving the crown downwardly from engagement with an upper tooth of a patient; and catching the crown in the basket should the crown become dislodged and fall from the grips of the dental device.

* * * * *